(12) United States Patent
Mansour

(10) Patent No.: US 8,751,256 B2
(45) Date of Patent: Jun. 10, 2014

(54) INTELLIGENT TOKENS FOR AUTOMATED HEALTH CARE INFORMATION SYSTEMS

(75) Inventor: Richard P. Mansour, Shreveport, LA (US)

(73) Assignee: Allscripts Software, LLC, Chicago, IL (US)

(*) Notice: Subject to any disclaimer, the term of this patent is extended or adjusted under 35 U.S.C. 154(b) by 133 days.

(21) Appl. No.: 12/658,698

(22) Filed: Feb. 11, 2010

(65) Prior Publication Data

US 2011/0196704 A1    Aug. 11, 2011

(51) Int. Cl.
*G06Q 10/00* (2012.01)
*G06Q 50/00* (2012.01)
*G06Q 50/24* (2012.01)

(52) U.S. Cl.
CPC ..................................... *G06Q 50/24* (2013.01)
USPC .................................................. 705/2; 705/3

(58) Field of Classification Search
CPC ....................................................... G06Q 50/24
USPC ......................................... 705/2–3; 715/500
See application file for complete search history.

(56) References Cited

U.S. PATENT DOCUMENTS

| 5,072,383 | A | 12/1991 | Brimm et al. ..................... 705/2 |
| 5,077,666 | A | 12/1991 | Brimm et al. ..................... 705/2 |
| 5,247,611 | A | 9/1993 | Norden-Paul et al. ........ 715/217 |
| 5,253,362 | A | 10/1993 | Nolan et al. .......................... 1/1 |
| 5,325,478 | A | 6/1994 | Shelton et al. ................ 715/236 |
| 2002/0120471 | A1* | 8/2002 | Drazen .............................. 705/3 |
| 2003/0120652 | A1 | 6/2003 | Tifft .................................. 707/6 |
| 2005/0010859 | A1* | 1/2005 | McDonough et al. ........ 715/500 |
| 2007/0294114 | A1* | 12/2007 | Urali et al. ........................ 705/3 |
| 2008/0215370 | A1* | 9/2008 | Dent et al. ........................ 705/3 |
| 2009/0024414 | A1 | 1/2009 | Mansour et al. .................. 705/3 |
| 2009/0164237 | A1* | 6/2009 | Hunt et al. ........................ 705/2 |

\* cited by examiner

*Primary Examiner* — Joseph Burgess
(74) *Attorney, Agent, or Firm* — Tillman Wright, PLLC; Chad D. Tillman; Jeremy C. Doerre

(57) ABSTRACT

Methods and systems for accessing information stored in an electronic patient record are disclosed. A memory stores a set of medical logic instructions which code for retrieval of multiple items of information stored in the electronic patient record for a given patient. Optionally, the instructions code for a rules-based interpretation of information stored in the electronic patient record, such as instructions that apply criteria in a quality scoring system and generate a score. The medical logic instructions are associated with an "intelligent token", i.e., a character string such as |DIABETES|, |ASTHMA| or |PROGRESS|. The invoking of the intelligent token triggers execution of the medical logic instructions and retrieval of the information from the database. The intelligent tokens can be embedded into document templates, or selected or entered by the user as part of a document creation process.

45 Claims, 11 Drawing Sheets

Fig. 5

Create | Preview

☐ Composite Section
  └ Interval Note

Document Info

Interval Note

✎Copy Forward | 📋 Refer To Note | ← Preview | 📋 Modify Template | A Acronym Expansion | |< | << | >> | >|

Hospital Day # 6, Hour #127 (current date and time : Jun 7, 2009 3:29)
—— IV Fluid Orders ——
5% dextrose +0.45% sodium chloride 1000 mL Intravenous <Continuous> @ 125 mL/hr, Give Over 8.08hr
—— Intake and Output ——
Mn/Dy/Year Time         Intake      Output      Net
Jun 7, 2009 7:00 am       240         500       -260
Jun 7, 2009 7:00 pm      2490        1645        845

The Intake and Output Totals for the last 24 hrs are:
                        Intake      Output       Net
                         2730        2145        585

Current Diet Orders: 1. Diet, Regular  2. NPO Diet

As of Jun 7, 2009 3:29pm Active Anticoagulant Orders:
1. enoxaparin injectable: 30 milliGRAM(s)  Every 12 hours  Subcutaneous
—— Recent Coagulation Studies ——
Jun 7, 2009 7:22 am       PT: (12.5)    INR: (1.1)
Jun 7, 2009 7:20 pm       PLT: (300)

Review of Temperature for the past 24 hours:
The maximum temp. was 101 recorded Jun 6, 2009 10:14 pm
The minimum temp. was 98.9 recorded Jun 7, 2009 4:00am
The recorded dates and times and temperatures are:
Jun 6, 2009 10:14 pm       (101)
Jun 6, 2009 10:27 pm       (101)
Jun 6, 2009 11:15 pm       (99)

130
120
102

Need Help? | ☐ Results Pending  ☐ Priority  ☐ Incomplete

Retrieve Last Charted Ver...
Insert Default Values
Clear Unsaved Data

Mark Note As:  ☐ Results Pending  ☐ Priority  ☐ Incomplete

☐ Calculate After Save     Cancel  Save  Save/Forward

Fig. 6

As of Jun 7, 2009 3:29 pm Active Anticoagulant Orders:
1. enoxaparin injectable: 30 milliGRAM(s) Every 12 hours Subcutaneous —— Recent Coagulation Studies ——
Jun 7, 2009 7:22 am    PT: (12.5)    INR:(1.1)
Jun 7, 2009 7:22 am    PLT: (300)

Review of Temperature for the past 24 hours:
The maximum temp. was 101 recorded Jun 6, 2009 10:14 pm
The minimum temp. was 98.9 recorded Jun 7, 2009 4:00 am
The recorded dates and times and temperatures are:
Jun 6, 2009 10:14 pm    (101)
Jun 6, 2009 10:27 pm    (101)
Jun 6, 2009 11:15 pm    (99)
Jun 7, 2009 4:00 am     (98.9)
Blood Cultures:
Jun 6, 2009 4:48 pm     Staphylococcus Aureus Cultures:
Jun 7, 2009 5:46 pm   Urine Culture (Cath)    E. Coli
Jun 7, 2009 4:48 pm   Blood Culture (Aero/Ana)   Staphylococcus Aureus
As of Jun 7, 2009 3:29 pm Active Antibiotic Orders:
1. piperacillin/tazobactam injectable 4.5 Gram(s) Every 8 hours Intravenous
2. CefTRIAXone: 2 Gram(s) Daily Intravenous piggy back
3. vancomycin: 1 Gram(s) Every 12 hours Intravenous piggy back
4. vancomycin: 1 Gram(s) Every 12 hours Intravenous piggy back

| Mn/Dy/Year Time     | WBC | Hgb | Hct | PLT |
|---------------------|-----|-----|-----|-----|
| Jun7, 2009 7:20 am  | 12  | 14  | 40  | 300 |
| Jun7, 2009 5:7 am   | 20  | 14  | 40  | 260 |
| Jun6, 2009 10:46 pm | 18  | 14  | 42  | 255 |

| Mn/Dy/Year Time     | Na  | K+  | CO2 | BUN | Cre |
|---------------------|-----|-----|-----|-----|-----|
| Jun7, 2009 5:14 pm  | 130 | 2.8 | 21  | 18  | 1.4 |

| Jun7, 2009 0:33 am  | 3.4 | Maximum K+ (3 days) |
| Jun7, 2009 3:7 pm   | 2.4 | Maximum K+ (3 days) |

| Jun7, 2009 0:33 am  | 2   | Maximum Creat (3 days) |
| Jun7, 2009 3:7 pm   | 0.8 | Maximum Creat (3 days) |

102

140

Create | Preview

Need Help?   Mark Note As: ☐ Results Pending  ☐ Priority  ☐ Incomplete   ☐ Calculate After Save   Save/Forward   Save   Cancel

Fig. 7

Interval Note

✓Copy Forward | 🔍 Refer To Note | ⬅ Preview | 🔧 Modify Template | 🔤 Acronym Expansion | |< | << | >> | >|

Hospital Day # 6, Hour #127 (current date and time : Jun 7, 2009 3:29)
— IV Fluid Orders —
5% dextrose +0.45% sodium chloride 1000 mL Intravenous <Continuous> @ 125 ml/hr, Give Over 8.08hr — Intake and Output —
| Mn/Dy/Year Time | Intake | Output | Net |
| Jun 7, 2009 7:00 am | 240 | 500 | -260 |
| Jun 7, 2009 7:00 pm | 2490 | 1645 | 845 |

The Intake and Output/Totals for the last 24 hrs are:
| Intake | Output | Net |
| 2730 | 2145 | 585 |

..blood

Current Diet Orders: 1. Diet, Regular  2. NPO Diet

As of Jun 7, 2009 3:29pm Active Anticoagulant Orders:
1. enoxaparin injectable: 30 milliGRAM(s) Every 12 hours Subcutaneous
— Recent Coagulation Studies —
Jun 7, 2009 7:22 am    PT: (12.5)    INR: (1.1)
Jun 7, 2009 7:20 pm    PLT: (300)

Review of Temperature for the past 24 hours:
The maximum temp. was 101 recorded Jun 6, 2009 10:14 pm Create | Preview
Sections
⊟ Composite Section
  └ Interval Note
Document Info Need Help?   Mark Note As: ☐ Results Pending  ☐ Priority  ☐ Incomplete Retrieve Last Charted Ver...
Insert Default Values
Clear Unsaved Data ☐ Calculate After Save    Save/Forward | Save | Cancel

Fig. 8

Sections: Composite Section — Interval Note

Interval Note

Copy Forward | Refer To Note | Preview | Modify Template | Acronym Expansion | |< << >> >|

Hospital Day # 6, Hour #127 (current date and time : Jun 7, 2009 3:29)
—— IV Fluid Orders ——
5% dextrose +0.45% sodium chloride 1000 mL Intravenous <Continuous> @ 125 mL/hr, Give Over 8.08hr —— Intake and Output ——
| Mn/Dy/Year Time | Intake | Output | Net |
|---|---|---|---|
| Jun 7, 2009 7:00 am | 240 | 500 | -260 |
| Jun 7, 2009 7:00 pm | 2490 | 1645 | 845 |

The Intake and Output Totals for the last 24 hrs are:
| | Intake | Output | Net |
|---|---|---|---|
| | 2730 | 2145 | 585 |

[RedCells Transfused]
[Platelets Transfused]
[FFP Transfused]

Current Diet Orders: 1. Diet, Regular  2. NPO Diet

As of Jun 7, 2009 3:29pm Active Anticoagulant Orders:
1. enoxaparin injectable: 30 milliGRAM(s) Every 12 hours Subcutaneous —— Recent Coagulation Studies ——
Jun 7, 2009 7:22 am    PT: (12.5)    INR: (1.1)
Jun 7, 2009 7:20 pm    PLT: (300)

Retrieve Last Charted Ver...
Insert Default Values
Clear Unsaved Data

Need Help?  Mark Note As:  ☐ Results Pending  ☐ Priority  ☐ Incomplete  ☐ Calculate After Save   Save/Forward | Save | Cancel

Fig. 9

Interval Note

□ Copy Forward | 🔍 Refer To Note | ← Preview | 📋 Modify Template | 🔤 Acronym Expansion | |< | << | >> | >|

Hospital Day # 6, Hour #127 (current date and time : Jun 7, 2009 3:29)
— IV Fluid Orders —
5% dextrose +0.45% sodium chloride 1000 mL Intravenous <Continuous> @ 125 ml/hr, Give Over 8.08hr — Intake and Output —
| Mn/Dy/Year Time | Intake | Output | Net |
|---|---|---|---|
| Jun 7, 2009 7:00 am | 240 | 500 | -260 |
| Jun 7, 2009 7:00 pm | 2490 | 1645 | 845 |

The Intake and Output Totals for the last 24 hrs are:
| | Intake | Output | Net |
|---|---|---|---|
| | 2730 | 2145 | 585 |

Red Cells Transfused during this admission:
Jun 7, 2009 10:51 am    Transfuse Packed Red Blood Cells - Units Ord: 1 Product   Packed Red Blood Cells Platelets Transfused during this admission:
Jun 7, 2009 10:52 am    Transfuse Platelets - Units Ord: 1 Instructions Single donor Fresh Frozen Plasma transfused during this admission:
Jun 7, 2009 10:51 am    Transfuse Fresh Frozen Plasma
Jun 7, 2009 10:52 am    Transfuse Fresh Frozen Plasma
Jun 7, 2009 10:53 am    Transfuse Fresh Frozen Plasma Current Diet Orders: 1. Diet, Regular  2. NPO Diet 160
162
164

Sections:
⊞ Composite Section
  └ Interval Note

Create | Preview
Document Info

Need Help? | □ Results Pending | □ Priority | □ Incomplete

Retrieve Last Charted Ver...
Insert Default Values
Clear Unsaved Data

Mark Note As: □ Calculate After Save | Save/Forward | Save | Cancel

Fig. 10

Hospital Day # 6, Hour #127 (current date and time : Jun 7, 2009 3:29)
--- IV Fluid Orders ---
5% dextrose +0.45% sodium chloride  1000 mL Intravenous <Continuous> @ 125 ml/hr, Give Over 8.08hr --- Intake and Output ---
| Mn/Dy/Year Time | Intake | Output | Net |
|---|---|---|---|
| Jun 7, 2009 7:00 am | 240 | 500 | -260 |
| Jun 7, 2009 7:00 pm | 2490 | 1645 | 845 |

The Intake and Output Totals for the last 24 hrs are:
| | Intake | Output | Net |
|---|---|---|---|
| | 2730 | 2145 | 585 |

Red Cells Transfused during this admission:
Jun 7, 2009 10:51 am    Transfuse Packed Red Blood Cells - Units Ord: 1  Product  Packed Red Blood Cells Platelets Transfused during this admission:
Jun 7, 2009 10:52 am    Transfuse Platelets - Units Ord: 1 Instrusctions Single donor Fresh Frozen Plasma transfused during this admission:
Jun 7, 2009 10:51 am    Transfuse Fresh Frozen Plasma
Jun 7, 2009 10:52 am    Transfuse Fresh Frozen Plasma
Jun 7, 2009 10:53 am    Transfuse Fresh Frozen Plasma Current Diet Orders: 1. Diet, Regular  2. NPO Diet As of Jun 7, 2009 3:29 pm Active Anticoagulant Orders:
1. enoxaparin injectable: 30 milliGRAM(s) Every 12 hours Subcutaneous --- Recent Coagulation Studies ---
Jun 7, 2009 7:22 am    PT: (12.5)    INR:(1.1)
Jun 7, 2009 7:22 am    PLT: (300)

INTELLIGENT TOKENS FOR AUTOMATED HEALTH CARE INFORMATION SYSTEMS

BACKGROUND

1. Field

This invention relates generally to the field of computerized medical records management systems, and in particular to methods of managing and recalling information from a medical records database for display to an end user using intelligent tokens.

2. Description of Related Art

In the medical arena, hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system often requires that one piece of information be entered into multiple records. In addition it often requires that the same information that has not changed from visit to visit (such as family/social history, allergies, immunization status) be re-asked of the patient and re-documented in the current record. In certain instances, such as in the Emergency Department, this information may be asked and recorded as many as three separate times (on the Triage Note; the main ED record; and MD documentation) leaving the patient to wonder if there is any communication between healthcare providers and frustrating those healthcare providers who must fill out more and more paperwork. If the patient is admitted, this same information is then asked and recorded again by the admitting nurse and attending physician.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside, particularly in a critical care environment. On the "flowsheet" chart there are individual areas for medication records, vital signs, intake/output, laboratory results, and other categories which are dependent upon the patient's affliction, such as intravenous (IV) drips.

Referring in particular to nursing functions, annotations to charts and/or nursing progress notes are made manually. Typically, brief notations are jotted down in various places through-out a shift. Sometime during the shift, typically at the end, the nurse makes a full notation into the nursing progress notes based on the brief notations or remembered items. This process can be very inefficient since notations may be forgotten or not copied appropriately. In particular, documentation and entry of physician orders, prescriptions and other activity has been viewed as two separate activities or steps, one step completing the documentation and a second step of entry of the order or prescription in the medical records of the patient.

The need for more efficiency of workflow and coordination between multiple departments and healthcare providers in a hospital environment has led to the advent of computerized, automated health care information systems. Such systems are known in the art, and include the systems disclosed in the following U.S. Pat. Nos. 5,325,478; 5,247,611; 5,077,666; 5,072,383 and 5,253,362 all assigned to the assignee of this invention, and have been commercialized by the Assignee of this invention and others.

In today's reimbursement regime, physicians, advanced practice nurses and physician assistants are required to create complex documentation regarding the episode of care and treatment in order to be reimbursed for professional services rendered to a patient. Heretofore, the creation of such documentation involved a condition-based chart review and manual construction and correlation of relevant information from an electronic patient record into a suitable format, requiring substantial amount of time and effort by the health care provider. This disclosure provides for automated features that allow for much more automated and rapid assembly of patient care information, and presentation in a suitable format, thereby providing substantial labor savings to health care providers and ultimately lower health care costs.

SUMMARY

In a first aspect, an automated health care information system is disclosed which includes a database storing an electronic patient record and a workstation having a user interface for displaying information stored in the electronic patient record. The display further including a display of a user interface tool for the user to enter or select, either directly or indirectly, an intelligent token. The intelligent token is a character string that is associated with a set of medical logic instructions. The medical logic instructions code for retrieval of multiple items of information stored in the electronic patient record for a given patient and/or a rules-based interpretation (i.e., creation or derivation of new information) of the stored information. In some embodiments, the medical logic instructions interpret or correlate the different items of information as may be required to make a medical assessment. The invoking (i.e., processing) of the intelligent token in the automated health care information systems triggers (1) execution of the set of medical logic instructions, and (2) retrieval of the multiple items of information stored in the electronic patient record. The invoking also typically triggers a display of such multiple items of information on the user interface.

Multiple intelligent tokens can be defined in the automated health care information system. For example, intelligent tokens can be defined that are associated with chronic disorders, acute care, or progress of a patient. For example, the system may include intelligent tokens for one or more of the following chronic disorders: 1) diabetes, 2) asthma, 3) hypertension, 4) a heart condition, 5) headache, and 6) a seizure disorder. Intelligent tokens for still other chronic disorders are of course possible. The intelligent tokens may also refer to or invoke still other tokens, including simple tokens and intelligent tokens.

As stated above, the intelligent tokens are associated with a set of medical logic instructions. The nature of the medical logic instructions can vary widely. Such instructions could be coded by a system administrator, vendor of the automated health care information system, or a chief medical officer (or the equivalent) of the user of the system.

Consider for example a situation where the intelligent token is associated with a chronic disorder such as asthma or diabetes. An example of such medical logic instructions linked to an intelligent token |DIABETES| are instructions which implement the following processing steps: Step 1: Search the electronic patient record of a patient and identify that chronic medical disorder exists. Step 2: Determine the duration of the chronic medical disorder by date subtraction (Today's Date minus Onset Date or Onset Year and Month). Step 3: Identify any associated conditions that may result from the primary condition. Example: Diabetes accelerates coronary artery disease and renal failure and retinal disease. Step 4: Perform a specific search of current medications that are used to treat this chronic medical condition. (Medication categories that are related to the chronic medical condition may be used as search criteria in order to identify the correct medications). Step 5: Search the electronic patient record for specific key performance indicators (e.g., blood pressure) related to the specific chronic medical condition. Obtain the latest measurement and date for such specific key performance indicators. Step 6: Apply specific criteria for Physician Quality Reporting Initiative (PQRI) or other quality scoring systems in existence today or to be later developed by any governmental body, or third party payer for medical care or private regulatory group, generate score, and return result. This step 6 may involve execution of rules-based medical logic module that creates new data from existing data in an electronic patient record. In essence, the medical logic instructions in step 6 implements a rules-based set of instructions which interpret information stored in the electronic patient record. As an example, such instructions apply criteria associated with a quality scoring system (e.g., PQRI) to information stored in the electronic patient record and responsively generate a score in the quality scoring system.

The manner in which the intelligent tokens can be invoked or triggered can vary depending on the environment in which they are used. In one possible example, the automated health care information system includes a documentation application for use in creating or displaying documentation regarding a patient, such as for example an interval or progress note, or a report for submission to a payor of health care services. The documentation application includes one or more templates. The intelligent tokens are present (possibly embedded and out of view from the user) in the templates. The user interface tool for the user to invoke the intelligent token is a user interface feature providing for the user to select one of the one or more templates.

As another example, the user interface tool for the user to invoke the intelligent token may take the form of a display of intelligent tokens available to the user and a feature by which the user may select one or more of the intelligent tokens. As another alternative, the user interface tool may take the form of a text box where the user may enter either the character string representing the intelligent token (e.g., |ASTHMA|) or a shorthand for the character string, such as .ASTHMA (i.e., the name of the token with a period before it, and without the beginning and ending characters|).

As still another example, the user may type the token or a shorthand for the character string directly into a document interface (e.g., in a preview document mode). When the user toggles to a create document mode in the interface the intelligent token is invoked, triggering execution of the medical logic instructions, retrieval of the information from the database and presentation of the information in the user interface.

In another aspect, health care apparatus is disclosed including a database storing an electronic patient record, a memory storing a set of medical logic instructions which code for retrieval of multiple items of information stored in the electronic patient record for a given patient, and a processing unit having access to the database for executing the medical logic instructions. The memory further stores an application comprising a set of software instructions for providing a user with access to information stored in the electronic patient record. The application includes a user interface tool for the user to invoke, either directly or indirectly, an intelligent token comprising a character string which is associated with the set of medical logic instructions. The invoking of the intelligent token triggering execution of the medical logic instructions by the processing unit.

The application or aspect of the automated hearth care information system which includes the intelligent token feature of this disclosure can take a variety of possible formats. Examples include a patient portal, wherein a patient can get access to their medical records, a provider-to-provider communications application for sharing information contained in the electronic patient record, and a medical documentation application. The triggering mechanism can take the forms described below, such as selecting of the intelligent token from a menu or list, entry into a text box, entry directly into a document, or through the use of templates.

In another aspect, a method of accessing information contained in an electronic patient record stored in a database is disclosed. The method includes the steps of associating a set of medical logic instructions with an intelligent token, the intelligent token comprising a character string, wherein the medical logic instructions code for retrieval of multiple items of information stored in the electronic patient record for a given patient; embedding the intelligent token into a template used for creation or display of medical documentation regarding the given patient; and triggering execution of the medical logic instructions in response to a user selection of the template.

In still another aspect, a method of accessing information contained in an electronic patient record stored in a database is disclosed. The method includes the steps of associating a set of medical logic instructions with an intelligent token, the intelligent token comprising a character string, wherein the medical logic instructions code for retrieval of multiple items of information stored in the electronic patient record for a given patient; displaying a list of intelligent tokens on a user interface of a workstation having access to the electronic patient record and a feature by which a user may select one or more of the intelligent tokens; and triggering execution of the medical logic instructions upon a user selection of one or more of the intelligent tokens.

In still another aspect, a method of accessing information contained in an electronic patient record stored in a database is disclosed comprising the steps of associating a set of medical logic instructions with an intelligent token, the intelligent token comprising a character string, wherein the medical logic instructions code for retrieval of multiple items of information stored in the electronic patient record for a given patient; providing a user interface tool on a workstation having access to the electronic patient record wherein the user may enter either the character string or a shorthand for the character string; and triggering execution of the medical logic instructions after a user has entered either the character string or a shorthand for the character string.

BRIEF DESCRIPTION OF THE DRAWINGS

Exemplary embodiments are illustrated in referenced figures of the drawings. It is intended that the embodiments and figures disclosed herein are to be considered illustrative rather than restrictive

FIGS. 5 and 6 are screenshots showing information returned from the database of FIG. 1 when the template of FIG. 4 is selected by a user.

FIG. 7 is a screenshot showing the |hospitalday| and |progress| token data with a shorthand for an intelligent token ".blood" inserted into the document by the user in order to invoke blood-associated medical logical modules associated with a |blood| token.

FIG. 8 is a screenshot showing the |hospitalday| and |progress| intelligent token data with three additional intelligent tokens related to blood inserted into the documentation; in this example the ".blood" shorthand was expanded to three blood-related intelligent tokens |RedCellsTransfused|, |plateletstransfused| and |FFPTransfused|.

FIG. 9 is a screenshot showing the |hospitalday| and |progress| intelligent token data along with the return of data associated with the three blood-related intelligent tokens inserted into the documentation.

FIG. 10 is a screenshot showing the |hospitalday| and |progress| intelligent token data along with the return of data associated with the three blood-related intelligent tokens inserted into the documentation; in FIG. 10 the user has toggled to a "preview" tab located in the upper left of the screenshot.

DETAILED DESCRIPTION

A. Overview

Figure 1:
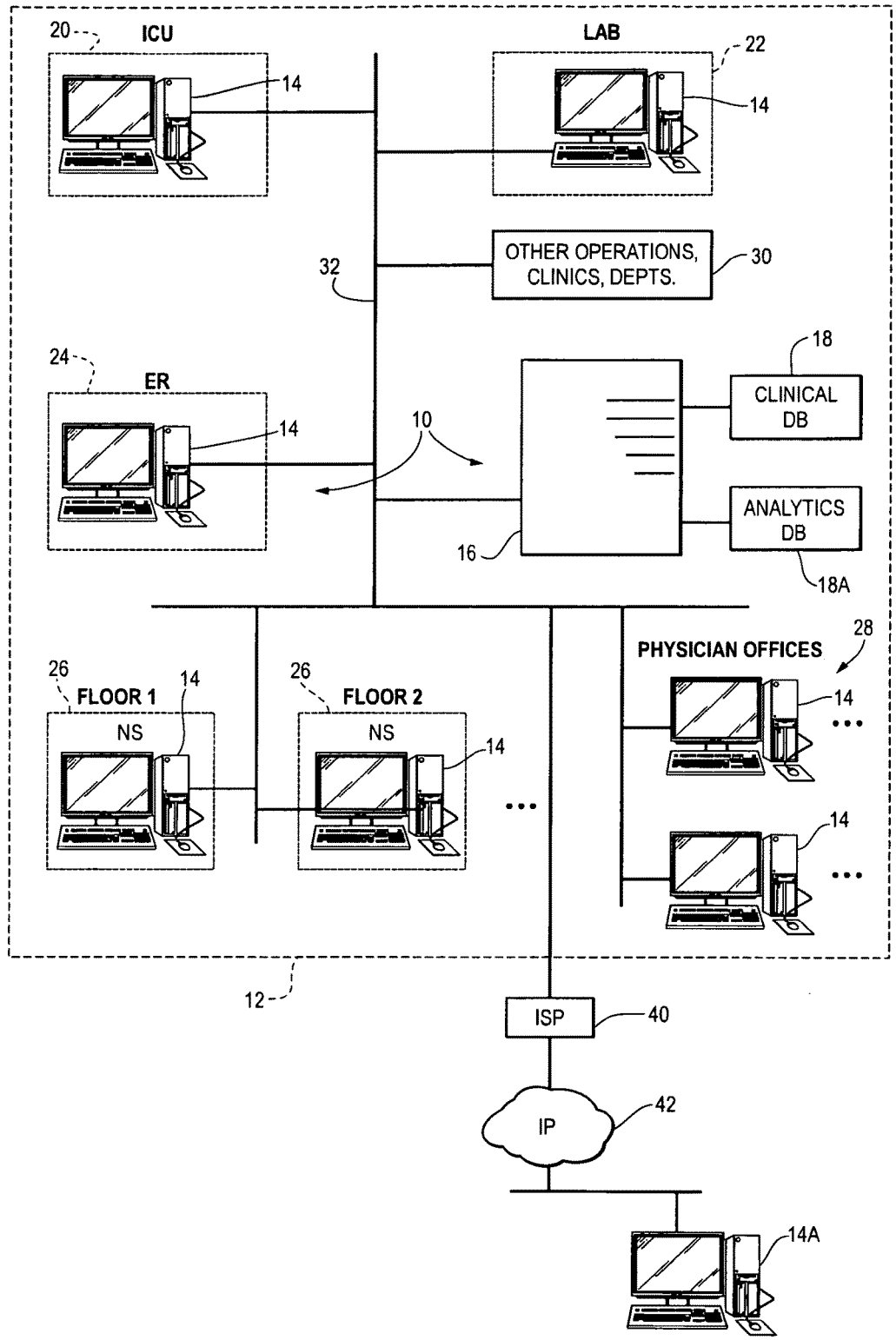
FIG. 1 is a block diagram of an automated health care information system storing electronic patient records for a plurality of patients served in a medical facility.

Referring now to FIG. 1, a representative and non-limiting example of an environment in which the invention can be practiced is shown in block diagram format. In particular, FIG. 1 depicts a computerized automated health care information system 10 that is used by clinicians (physicians, nurses and other medical personnel) and hospital administration. The system is shown installed in a medical facility 12 indicated in dashed lines. The medical facility may for example be a hospital, nursing home, clinic, or other medical enterprise. The details on the medical enterprise and type of health care services it may render to patients are not particularly important. A typical application of this invention is the hospital environment, and therefore the following description will be made in conjunction with a hospital.

The automated health care information system 10 includes a plurality of distributed workstations or client computers 14, a central database server 16 and a clinical database 18A containing electronic patient records. An analytics database 18B also stored clinical information and is used for analyzing data in the patient records as explained in the co-pending U.S. application Mansour et al. Ser. No. 11/879,664 filed Jul. 17, 2007, the content of which is incorporated by reference. The workstations 14 could be for example general purpose computers with a processing unit and graphical display unit. The workstations 14 could also be hand-held computers. The workstations 14 include a memory storing an interactive, client-server based patient documentation application that is executed by the processor in the workstation. The application provides user interface tools in the form of graphical screen displays which allow the user access the electronic patient records stored in the database, review and create progress notes, add clinical documentation, or otherwise access an electronic patient record of a patient being treated at the facility 12.

As shown in FIG. 1, the facility 12 may include an Intensive Care Unit 20 with a workstation 14, which may be used by ICU physicians and ICU nurses to access patient records and input orders, write prescriptions, view patient allergies, and input documentation. The facility may also include one or more laboratories 22, each of which may include a workstation. Lab personnel may input test results into the patient record stored in the database 18. The facility may also include an Emergency Room (ER) 24, where a workstation 14 is provided for ER clinicians to records and input orders, write prescriptions, view patient allergies, note significant events and chief complaints of the patients and input them into the electronic patient record stored in the database 18. The facility may also have a number of patient rooms and provide nurses stations (NS) 26 on each floor, each of which has a workstation 14. Additionally, physicians' offices 28 may also include workstations 14, in the form of personal computers. The facility 12 may have other operations, clinics, departments, etc. as indicated at 30, each of which may be provided with additional workstations. The workstation are networked on a local area network 32 wherein all of the workstations may exchange data with the central database server 16 and thereby access the patient records stored in the database 18A and write documentation and orders, prescriptions, and other information to the database 18A.

The network 32 may include a router (not shown) providing a connection to an internet service provider (ISP) 40 providing access to an external wide area internet protocol network 42 such as the Internet. A workstation 14A may be coupled to the enterprise network 32 via the ISP 40 whereby a clinician authorized to access patient records in the database 18 may do so via the Internet 42, ISP 40 network access server and local area network 32. Thus, a workstation 14, 14A creating patient documentation need not necessarily physically reside on the network 32 or be physically located within or at the enterprise 12.

Thus, the automated health care information system 10 that is installed in the medical facility 12 allows clinicians to access patient records in a medical records database 18A. The system 10 may take the form of automated health care information systems known in the art and commercially available from Eclipsys Corporation, Siemens, and others. The preferred embodiment of such a system provides clinicians information they need, when and where they need it—at the point of care (e.g., in the ER or at the nursing stations 26), in the offices 28, even at home via a computer 14A and the Internet 42.

Figure 2:
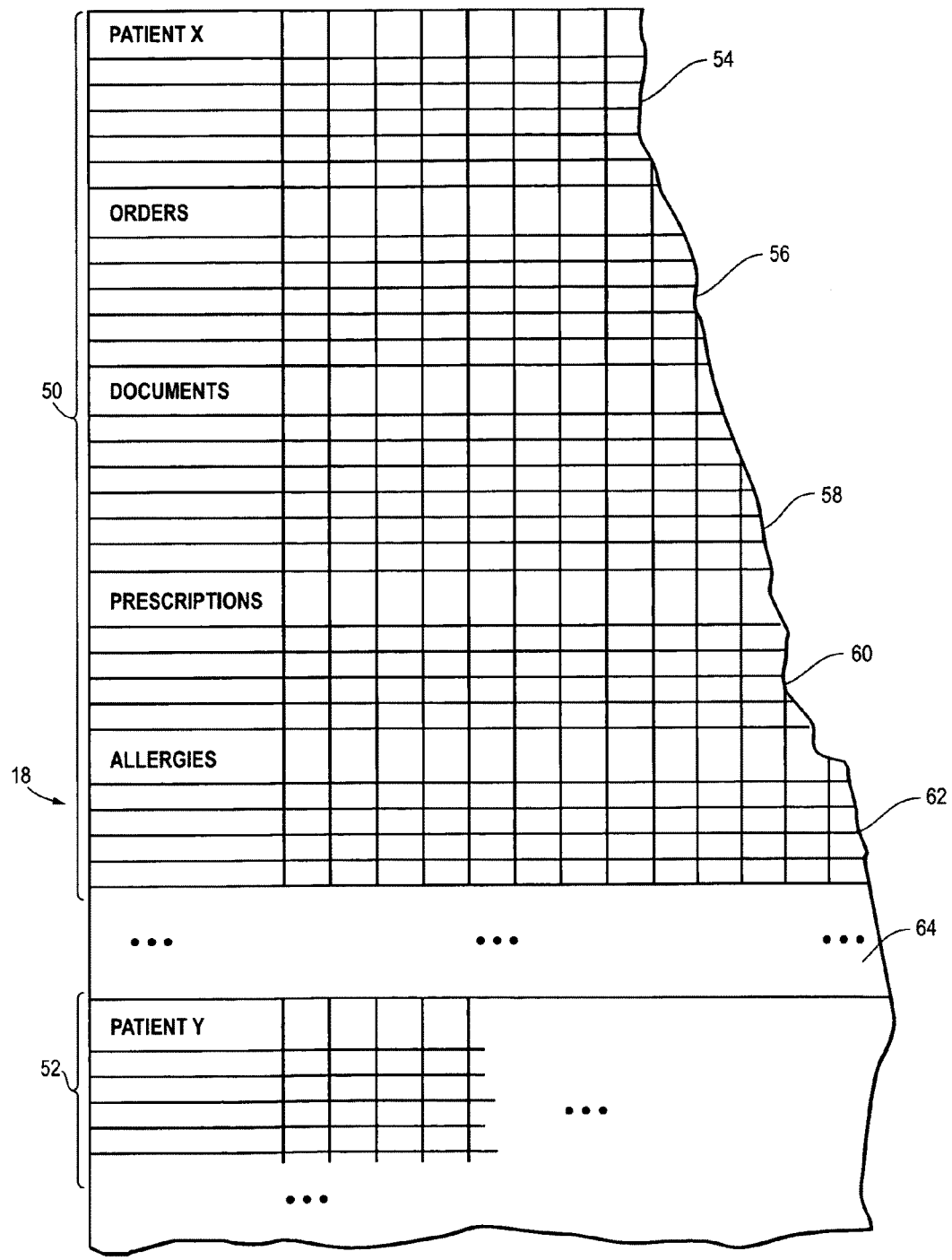
FIG. 2 is a schematic representation of the clinical database of FIG. 1.

A schematic representation of the database 18A is shown in FIG. 2. The database includes a multitude of electronic patient records 50, 52 each comprising rows and columns of data. A first field 54 of the record is directed to patient information, such as the name, address, gender, insurance carrier, date of birth, etc.

A second field 56 contains orders for the patient. The orders are determined by health care personnel treating the patient.

Each row in the orders field 56 may constitute a specific order, and the various columns in the row devoted to different aspects of the order, such as the entering physician's name, the type of order, the date it was placed, etc.

A third field 58 is directed to documents (i.e., documentation) entered by a physician or nurse. Each row may represent specific instances of documentation created by a user.

A fourth field 60 contains outpatient prescription medications the patient is taking and any in-patient prescriptions that are ordered for the patient.

A fifth field 62 contains data of all the patient's allergies.

Other fields 64 are also present, and may include fields devoted to significant events, health issues (problem list), care providers and others. The name of the categories in the electronic patient record, and the number of categories is not particularly important and may vary depending on the environment and the choices made by a system administrator.

With the above overview and background in mind, this disclosure will now proceed to discuss the creation of medical documentation using tokens, including simple tokens and intelligent tokens.

Simple Tokens

The term simple "token", as used in this document, is intended to refer to a sequence of characters that represent one or more pieces of data. When a simple token is processed by a software program, the token is replaced by the data it represents, if such data exists. The data is typically retrieved from a database. For example, in the medical records art, the token |age| is a placeholder representing the age of a patient. The token |name| is a placeholder for the name of the patient. The first and last characters of a token may include special characters, including other tokens, for example the token |age|.

As an example of how simple tokens such as |name| or |age| are used, consider an instruction of the following form that is interpreted by a medical records information system:

|name| is a |age| patient

This instruction would be interpreted as a command to retrieve the patient's name and age from the medical records of the patient. The following line of text would be rendered in response to the instruction:

John Smith is a 56 year old patient.

An example of a list of simple tokens that may be supported by an automated medical records information software system is shown in Table 1.

TABLE 1

| Token | Association |
|---|---|
| \|chiefcomplaint\| | the patient's chief complaint |
| \|allergy\| | any allergies of the patient |
| \|problems\| | current illnesses or medical problems of the patient |
| \|vitals\| | current vital signs of the patient |
| \|omp\| | Outpatient Medication Profile, i.e., current active prescriptions for the patient |
| \|name\| | patient's name |
| \|age\| | patient's age |
| \|gender\| | patient's gender |

Figure 3:
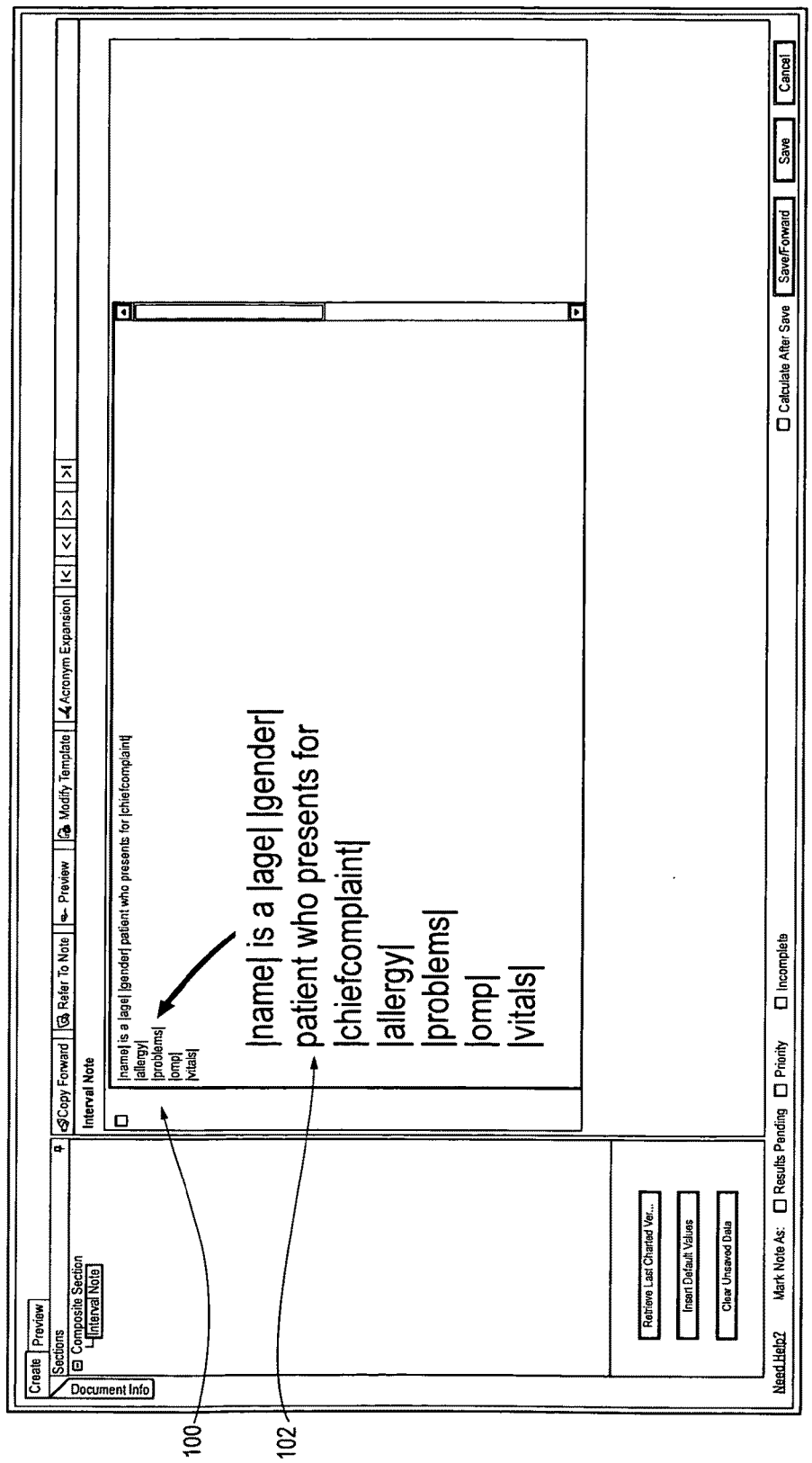
FIG. 3 is a screen shot displayed on a workstation in the system of FIG. 1 showing a template for creating an interval note (i.e., patient documentation), in which the template includes simple tokens such as tokens for the name, age and gender of the patient.

An example of the use of simple tokens will be explained in conjunction with FIG. 3. FIG. 3 is a screen shot displayed on a workstation of FIG. 1 which displaying a template by which a user (e.g., physician) can create an interval (progress) note for a given patient. The interval note is a summary of relevant patient information. FIG. 3 shows that the template has embedded simple tokens (which not visible to the user but are shown in FIG. 3). When the user selects "interval note" (by a drop down menu list, radio button, tab, text entry box, or other feature identifying interval note, the template with embedded tokens is retrieved. The simple tokens are shown in FIG. 3 to illustrate the content of one of such templates. The template includes the following plain text and simple tokens delimited by the |character:

|name| is a |age| |gender| patient who presents for |chiefcomplaint|
|allergy|
|problems|
|omp|
|vitals|

When the template of FIG. 3 is selected by the user, the document writing software associated with interval note shown in FIG. 3 interprets (i.e., processes) the simple tokens in the template and automatically retrieves the associated information directly from the relevant fields in the patient's electronic medical record, namely the patient's name, age, gender, chief complaint, allergies, problems, outpatient medication profile ("omp"), and vital signs. The resulting information is displayed in a user-friendly format in the window 102.

The use of simple tokens like the ones in Table 1 have limited usefulness in terms of facilitating a physician viewing a medical record, or facilitating a physician creating documentation regarding a patient, such as a progress or interval note. This disclosure provides for methods and apparatus for overcoming these limitations by means of the use of "intelligent tokens."

Intelligent Tokens

This disclosure features the use of an improved medical document writing token which is referred to herein as an "intelligent token." The intelligent tokens can be used for several purposes, including rapid synthesis of the current state of a chronic medical condition and presentation of such information to an end user. In essence, the term "intelligent token" is used to refer to a character string, e.g., |DIABETES|, which is associated with a set of medical logic instructions. The medical logic instructions code for retrieval of multiple items of information stored in an electronic patient record (FIG. 2) for a given patient and/or a rules-based interpretation (i.e., creation or derivation of new information) of the stored information. The interpretation of an intelligent token, e.g., by a medical records software module, triggers execution of the associated medical logic instructions and retrieval of the multiple items of stored information and/or a rules-based interpretation of the stored information and display of said stored information and interpreted information in a user interface. An examples of a rules-based interpretation of stored information is the generation of grading scores for key patient care performance indicators through the use of quality scoring algorithms encoded in the medical logic instructions.

For example, the intelligent tokens are used to display such information on a user interface of one of the workstations of FIG. 1, as part of a medical document writing exercise or review of a patient's electronic patient record. Examples of the structures, usage, and events for triggering the interpretation of the intelligent token are explained below.

The precise nature of the medical logic modules (program code) that is associated with a given intelligent token can vary widely. Such medical logic modules typically will be authored or coded by an administrator of the automated health care information system which uses such tokens, or possibly by the vendor of such a system. The system may also grant permissions to certain individuals within the organization using the system to author or modify such modules. In general, intelligent tokens are designed to retrieve, organize and display a pertinent package of information following a specific search, retrieve, interpret, and collate strategy such that the output of the intelligent token is of maximum usefulness to the end user.

In one example, intelligent tokens can be associated with a chronic disorder, acute care, a patient's current medical status, or other aspect of patient care, status or treatment. In one example, the intelligent token is associated with a chronic disorder. For example, the automated health care information system of FIG. 1 defines intelligent tokens for each of the following chronic disorders: 1) diabetes, 2) asthma, 3) hypertension, 4) a heart condition, 5) headache, and 6) a seizure disorder. Intelligent tokens for still other chronic disorders can be created, of course. The medical logic modules which are associated with each of such chronic medical disorders will of course vary, and be specific to the particular chronic disorder. In one possible embodiment, the medical logic instructions retrieve multiple items of information from the electronic patient record, such as a duration associated with the disorder, associated conditions of the disorder, specific treatments for the disorder, performance indicators associated with the disorder, and grading scores for the performance indicators.

In one specific example of an intelligent token for a chronic medical disorder, the medical logic modules essentially code a search, retrieve, interpret, and collate strategy. This functionality can be coded in the medical logic modules as a series of steps:

Step 1: Search the electronic patient record of a patient and identify that chronic medical disorder exists.

Step 2: Determine the duration of the chronic medical disorder by date subtraction (Today's Date Minus Onset Date or Onset Year and Month)

Step 3: Identify any associated conditions that may result from the primary condition. Example: Diabetes accelerates coronary artery disease and renal failure and retinal disease.

Step 4: Perform a specific search of current medications that are used to treat this chronic medical condition. (Medication categories that are related to the chronic medical condition may be used as search criteria in order to identify the correct medications)

Step 5: Search the electronic patient record for specific key performance indicators (e.g., blood pressure) related to the specific chronic medical condition. Obtain the latest measurement and date for such specific key performance indicators.

Step 6: Apply specific criteria for Physician Quality Reporting Initiative (PQRI) or other quality scoring systems in existence today or to be developed by any governmental body, or third party payer for medical care or private regulatory group and return result. This step may involve execution of rules-based medical logic module that creates new data from existing data in an electronic patient record.

In one possible embodiment, the intelligent tokens thus combines the retrieval of disease or condition specific medical data from an electronic patient record and correlates it to additional specific types of data and generates new data through the use of quality scoring algorithms. The medical logic instructions associated with the intelligent token can incorporate a medical assessment strategy developed for each intelligent token assigned to a chronic disease or condition. Unlike simple tokens, intelligent tokens do not simply replace a place holder with a piece of data; rather, they can be used to orchestrate the synthesis of condition-specific complex medical assessments and associations that requires many steps embedded with advanced medical knowledge (see, for example, the six steps discussed above). By encapsulating this advanced medical knowledge into coded medical logic instructions, the assembly of such assessments and information can be performed in an automated fashion, saving health care practitioners from the task of assembling this information manually, and thus providing a substantial labor savings and ultimately lowering health care costs.

Examples of how intelligent tokens may be structured and arranged are set forth below. An automated health care information system defines an intelligent token for each of several chronic disorders, such as for example diabetes, hypertension, asthma, heart condition, headache, and a seizure disorder. Each of the above intelligent tokens for chronic |disorders is associated with medical logic modules (program code) that retrieve or interpret multiple items of information from an electronic patient record following any or all of the six steps outlined above.

Example 1

Intelligent Token |DIABETES|

Consider for example an intelligent token |DIABETES|. When this intelligent token is interpreted, associated medical logic modules are executed and the following information is retrieved from the electronic patent record and presented on a workstation in conjunction with the creation or review of a progress note or other type of medical documentation:

Diabetes:

The diagnosis of type II diabetes was established Nov. 2002 (duration 7 years).

—Diabetes Medications—:

1. glyBURIDE tablet 5 mg: 1 tab(s) orally once a day×30 days
2. metformin tablet, extended release 1000 mg: 1 tab(s) orally once a day The most recent Hemoglobin A1c level is 8.3 (performed on Nov. 1, 2009)

The most recent Low Density Lipoprotein level was 100 (performed on Nov. 1, 2009)

In this example, the medical logic modules associated with the |DIABETES| intelligent token did not retrieve any Associated Conditions, because there were none present in the electronic medical record for the patient. The Specific Treatments are the diabetes medications that were listed. The Key Performance Indicators were the Hemoglobin and LDL levels that were reported. There were no Grading Scores retrieved in this example.

Example 2

Intelligent Token |HYPERTENSION|

Consider in this example an intelligent token |HYPERTENSION|. The intelligent token |HYPERTENSION| is associated with medical logic modules which retrieve or derive the following items of information from an electronic patient record, if present: Disease or Condition, Duration, Associated Conditions, if any, that are present, Specific Treatments, Key Performance Indicators and Grading Scores for Key Performance Indicators. When this intelligent token is interpreted the following information is retrieved or derived for a given patent and output on the display of a workstation:

Hypertension:

The diagnosis of Hypertension established Nov. 2003 (duration 6 years).

Active Medical Therapy:

1. Altace capsule 5 mg, quantity: 30, refills: 3, Ref: Nov. 16, 2009.

The most recent Systolic Blood Pressure was 141.

The most recent Diastolic Blood Pressure was 89.

Thus, the output of this intelligent token is the disease or condition (HYPERTENSION), the duration (expressed as both the date the diagnosis was established and the duration), specific treatments (Altace 5 mg), and Key performance indicators (systolic and diastolic blood pressures).

Example 3

Intelligent Token |ASTHMA|

In this example, the intelligent token is |Asthma|. The intelligent token |Asthma| is associated with medical logic modules which retrieve or derive the following items of information from an electronic patient record, if present: Disease or Condition, Duration, Associated Conditions, if any, that are present, Specific Treatments, Key Performance Indicators and Grading Scores for Key Performance Indicators. For example for a given patient the following may be the output of the intelligent token |ASTHMA|:

Asthma:

The diagnosis of Asthma established Nov. 2006 (duration 3 years).
—Systemic Steroids—:
1. Pulmicort Flexhaler 90 mcg/inh inhalation powder: 1 puff(s) inhaled 2 times a day
—Relievers—:
1. albuterol 0.63 mg/3 mL (0.021%) inhalation solution: 3 mL inhaled 4 times a day as needed for Shortness of Breath
—Controllers—:
1. montelukast tablet, chewable 4 mg: 1 tab(s) chewed once a day (in the evening)×30 days
2. Pulmicort Flexhaler 90 mcg/inh inhalation powder: 1 puff(s) inhaled 2 times a day.

In this example, there were no associated conditions, key performance indicators or grading scores which were returned.

This disclosure further contemplates additional types of intelligent tokens, including what are referred to herein interchangeably as a "complex token" or "complex intelligent tokens". Complex tokens are associated with a set of medical logic instructions which perform an instant, automatic chart review, return of relevant information, and grouping of related system-level information together for a medical note. As an example, a Complex Token |CULTURE| is associated with medical logic modules (program code) that implement the following steps:

Step 1: Acquire Body Temperature Information
Step 2: Obtain Blood and Urine Culture Information
Step 3: Obtain Current Antibiotic Information
Step 4: Correlate these three types of data
Step 5: Synthesize and summarize a statement about this data for inclusion in a medical documentation or progress report user interface.

Example 4

Complex Intelligent Token |ACUTE CARE|

A complex intelligent token |ACUTE CARE| is associated with medical logical modules that code the following operations:
1. Review the Chart
2. Group System status items together, such as for example Intake/Output
    IV Fluid Orders
    Diet Order
OR
    Temperature Pattern
    Culture Results
    Antibiotics Therapy
OR
    Coagulation Lab
    Anticoagulant Therapy When the intelligent token |ACUTE CARE| is interpreted, the modules executed and the pertinent information is retrieved from the database. The output of the intelligent token is presented on the user interface of a workstation in the system, e.g., in the body of a medical progress note or patient documentation interface.

Examples of the use and display of the outputs of intelligent tokens will now be described in the context of FIGS. 4-11.

Figure 4:
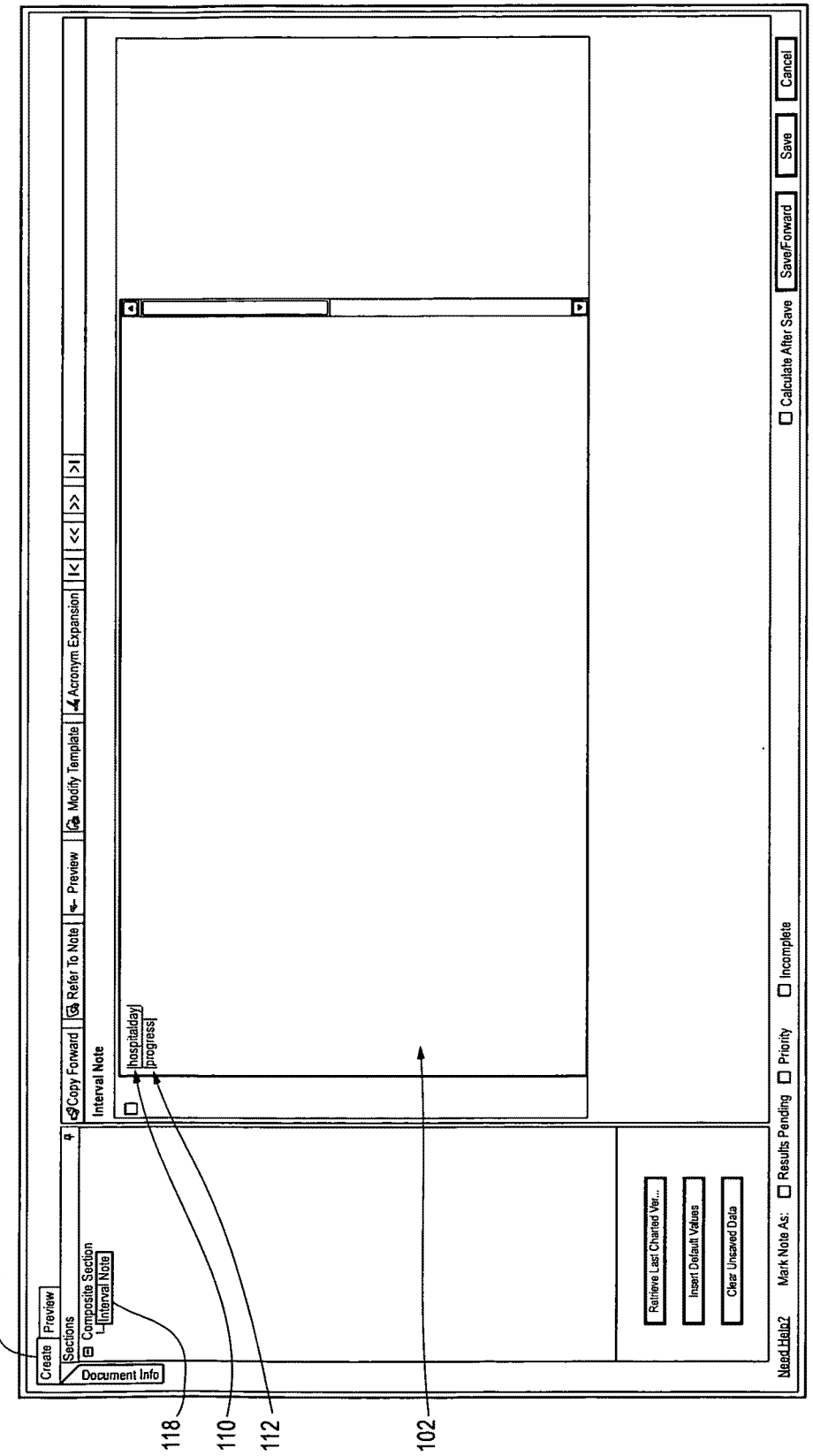
FIG. 4 is a screen shot displayed on a workstation showing a template for creating an interval note (i.e., patient documentation), in which the template includes intelligent tokens; in the example of FIG. 4 two tokens are present in the template, namely |hospitalday| and the complex intelligent token |progress|.

FIG. 4 is a screen shot displayed on a workstation 14 of FIG. 1 showing a template for creating an interval note (i.e., patient documentation), in which the template includes intelligent tokens. In the example of FIG. 4 two intelligent tokens are present in the template, namely |hospitalday| 110, and the complex intelligent token |progress| 112. When the template of FIG. 4 is selected, e.g., by clicking highlighting the CREATE tab 116 and clicking on the interval note icon 118, the template is retrieved from memory, parsed for presence of the intelligent tokens, and then when they are recognized the associated medical logic instructions with each intelligent token is executed. The resulting information is returned from the database, organized as dictated by the code, and presented in the main window 102.

FIGS. 5 and 6 are screenshots showing information returned from the database of FIG. 1 when the template of FIG. 4 is selected by a user. FIG. 6 is a continuation of the information presented in FIG. 5 by scrolling down using the scroll tool 130. The intelligent token |hospitalday| 110 of FIG. 4 is associated with medical logic instructions which code for retrieval of the first line of information 120 in FIG. 5. In particular, the medical logic instructions associated with |hospitalday| 110 search the electronic patient record and determine how many days, and how many hours, the patient has been admitted to the hospital. The instructions also return the current date and time.

The complex intelligent token |progress| 112 of FIG. 4 is associated with medical logic modules which return the information shown in the window 102 other than the line 120. The medical logic modules associated with the |progress| token perform an instant, automatic chart review, return of relevant information, and grouping of related system-level information together for a medical note In this example, the instructions return a summary of the patients current status, including IV fluid orders, intakes and outputs, diet orders, temperatures, culture test results, antibiotics, anti-coagulants, clotting blood tests, and multiple types of other blood tests. This information is displayed in a organized, logical manner with appropriate headings in the main window 102 in FIGS. 4 and 5.

In FIG. 6, the user has toggled to the PREVIEW tab, which provides a view of the data as it would appear if the user elected to print out the displayed medical document (interval or progress note).

FIG. 7 is a screenshot showing the |hospitalday| and |progress| intelligent token data with the user toggled to the CREATE tab in the upper left hand corner. The user has reviewed the report and entered directly into the document via the keyboard a shorthand character string ".blood" 150 in order to trigger execution of medical logic instructions that are associated with the intelligent token |blood|. The vertical line 152 in this example is the cursor symbol, not a character string which is part of the shorthand. This screen shot thus illustrates additional flexibility that is provided to the user to enter and use intelligent tokens: they simply enter them (or a shorthand for them) directly into a medical document, e.g., when in a document create mode. When the user toggles to the preview mode (by activating the preview icon 140), the code for the documentation application parses the document displayed in FIG. 7 for the presence of intelligent tokens, detects the ".blood" shorthand, and triggers execution of medical logic modules associated with the |blood| intelligent token.

It will be appreciated that the methodology of FIG. 7 of entering intelligent tokens can be applied to any token, including simple tokens, intelligent tokens such as tokens associated with acute care or chronic disorders, or complex intelligent tokens.

FIG. 8 is a screenshot showing the |hospitalday| and |progress| intelligent token data with three additional intelligent tokens related to the .blood shorthand inserted into the documentation. In this example the ".blood" shorthand is linked to three intelligent tokens, and is expanded to recite them: |RedCellsTransfused|, |plateletstransfused| and |FFP-Transfused|. Each one of these intelligent tokens is associated with medical logic modules which code for retrieval of information related to red blood cells transfused, platelets transfused, and fresh frozen plasma (FFP) transfused, respectively.

FIG. 9 is a screenshot showing the |hospitalday| and |progress| intelligent token data along with the return of data associated with the three blood-related intelligent tokens inserted into the documentation, shown as entries 160, 162 and 164, respectively.

FIG. 10 is a screenshot showing the |hospitalday| and |progress| intelligent token data along with the return of data associated with the three blood-related intelligent tokens inserted into the documentation; in FIG. 10 the user has toggled to a "preview" tab 140 located in the upper left of the screenshot.

Figure 11:
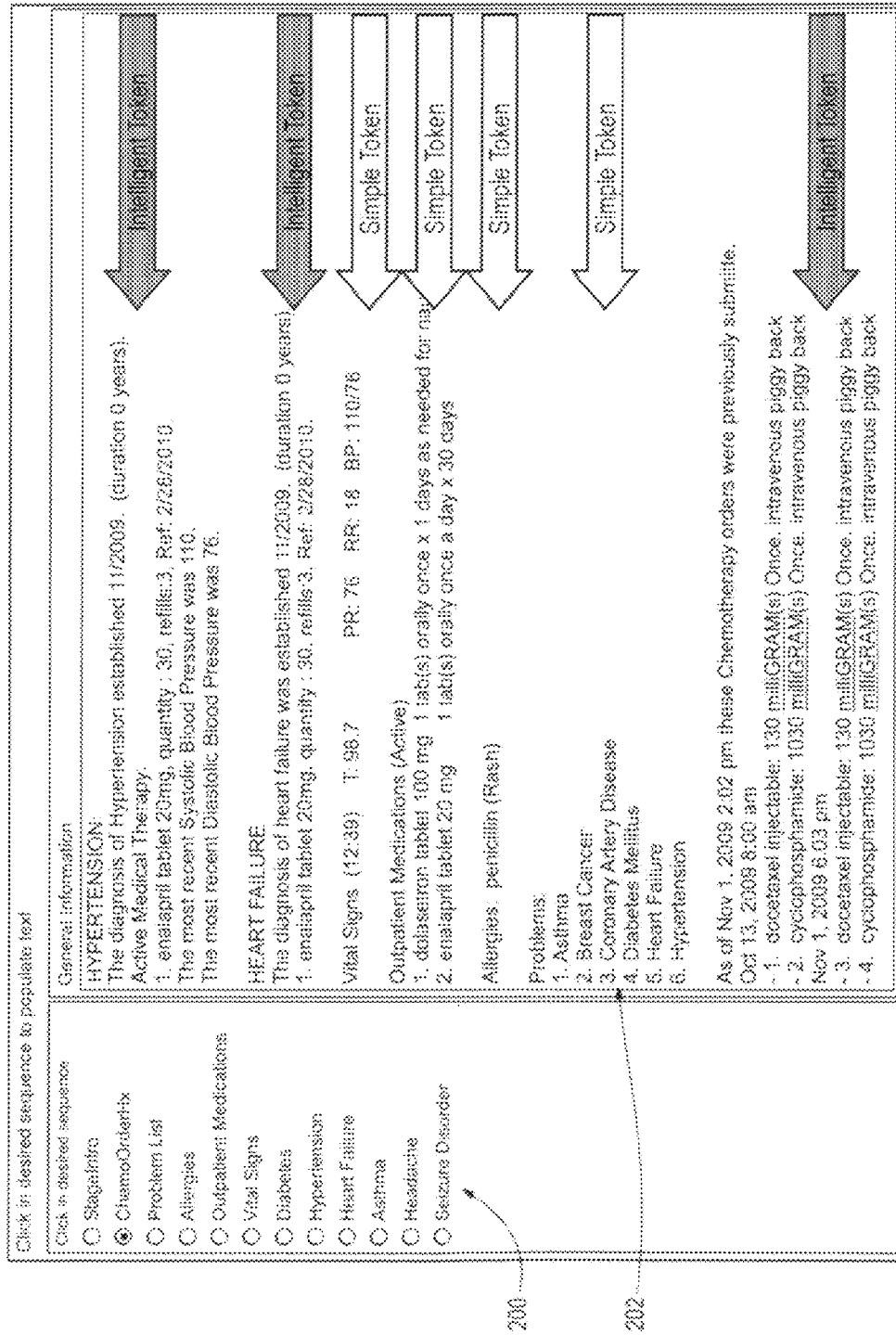
FIG. 11 is a screenshot showing a user with the option to select a combination of simple tokens and intelligent tokens on the left hand side of the screen, and in the main window the information that is retrieved from the database depending on the sequence of simple and intelligent tokens selected by the user.

FIG. 11 is a screenshot showing a user interface on a workstation in the system of FIG. 1, displaying the option to select a combination of simple tokens and intelligent tokens on the left hand side of the screen 200, and in the main window 202 the information that is retrieved from the database depending on the sequence of simple and intelligent tokens selected by the user. The user selects the tokens displayed in the left hand side 200 in any desired sequence. The document creation application then invokes the resulting medical logical modules associated with the intelligent tokens and returns the data from the database associated with the simple tokens. The retrieved data is then presented in window 202 is then presented in order of the sequence of tokens selected by the user. In this example, the user selected tokens in the following sequence:

Intelligent token Hypertension
Intelligent token Heart Failure
Simple token Vital Signs
Simple token Outpatient Medications
Simple token Allergies
Simple token Problem List
Intelligent token ChemoOrdersHx
Example of Medical Logic Modules When a template, document or other type of file structure is processed by the automated health care information system, the system searches for the character string identifying the intelligent token. If one is found, then associated medical logic modules are called. An example is set forth in the following pseudo code:

```
...
ELSEIF token_name = "|hypertension|" then
    disease_management:=
    MLM 'Called_TOKEN_Hypertension_HI';
    return_string := CALL disease_management WITH Client_guid ;
ELSEIF token_name = "|diabetes|" then
    disease_management:= MLM 'Called_TOKEN_DM_HI';
    return_string := CALL disease_management WITH Client_guid ;
/*
    In the |diabetes| example,
    Called_TOKEN_DM_HI Calls the following MLMs
    (medical logic modules)
        1. Called_Guideline_TOKEN_MLM
        2. Called_MLM_Observation_Data
        3. Called_TOKEN_EST_CRCL
        4. Called_Wellenss_Manager_Events_TOKEN_MLM
*/
```

Other Applications of Intelligent Tokens

This invention has utility in any medical records application which involves physician documentation.

The product of the intelligent token features of this disclosure meets the E&M coding requirements for documenting chronic medical conditions in the "History of Present Illness" Documentation Guideline. Additional, it meets the E&M coding requirements for documenting complex medical decision making for the "Medical Decision Making" Documentation Guideline.

The invention also has uses in medical communications from provider to provider, as for example in automated letters and secure health messages. For example, the intelligent tokens can be inserted into automated letters and secure health messages, or inserted into template automated letters and template secure health messages. When the automated letter or secure health messages are created or transmitted, the intelligent tokens are interpreted, triggering execution of the associated medical logic modules and assembly of the information from the electronic patient records into the automated letter or secure health message.

Additionally, the invention has uses in a patient portal for provider-to-patient communications. For example, in a secure web-based portal, a web page devoted to patient treatment information can be coded in a markup language which is augmented to provide for interpretation and rendering of intelligent tokens. When the web page is requested by a patient client station, a web server parses the web page markup language coding for the presence of intelligent tokens. Detection of the tokens triggers execution of the associated medical logic modules. The resulting information retrieved from the electronic patient record is inserted into the page and transmitted to the patient's client station.

Additional examples of where the intelligent tokens have usefulness are in home health care note writing (i.e., stand-alone medial records applications where patient information is stored locally on a laptop PC used by a home health care provider). Other examples include automated chart abstraction for quality reporting, automation of the writing of physician progress notes for inpatient and ambulatory care. The intelligent token feature is specifically well suited to software applications directed to clinical management of acute care, ambulatory patient care, and emergency department care.

Methods of Use and Invoking Intelligent Tokens

A number of different ways of invoking or using intelligent tokens, including using templates, direct entry of tokens into a medical document, or selection of intelligent tokens from a menu or list of displayed tokens.

In one possible embodiment, the invention can be viewed as method of accessing information contained in an electronic patient record stored in a database, comprising the steps of: associating a set of medical logic instructions with an intelligent token, the intelligent token comprising a character string, wherein the medical logic instructions code for retrieval of multiple items of information stored in the electronic patient record for a given patient; embedding the intelligent token into a template used for creation or display of medical documentation regarding the given patient; and triggering execution of the medical logic instructions in response to a user selection of the template.

In another aspect, the invention can be viewed as a method of accessing information contained in an electronic patient record stored in a database, comprising the steps of: associating a set of medical logic instructions with an intelligent token, the intelligent token comprising a character string, wherein the medical logic instructions code for retrieval of multiple items of information stored in the electronic patient record for a given patient; displaying a list of intelligent tokens on a user interface of a workstation having access to the electronic patient record and a feature by which a user may select one or more of the intelligent tokens; and triggering execution of the medical logic instructions in a processing unit in response to a user selection of one or more of the intelligent tokens.

In still another example, the invention can be viewed as a method of accessing information contained in an electronic patient record stored in a database, comprising the steps of: associating a set of medical logic instructions with an intelligent token, the intelligent token comprising a character string, wherein the medical logic instructions code for retrieval of multiple items of information stored in the electronic patient record for a given patient; providing a user interface tool on a workstation having access to the electronic patient record wherein the user may enter either the character string or a shorthand for the character string (e.g., directly into a medical document or into a text box providing for user entry of an intelligent token character string), and triggering execution of the medical logic instructions in response to the user entry of the character string or a shorthand for the character string.

In these methods, as explained above, the intelligent token may be associated with medical logic instructions which implement a rules-based interpretation of information stored in the electronic patient record. For example, the medical logic instructions comprise instructions which apply criteria associated with a quality scoring system to information stored in the electronic patient record and responsively generate a score in the quality scoring system.

In these methods, the intelligent token can be associated with at least one of a) a chronic disorder; and b) acute care and c) a patient's current medical status. For example the intelligent tokens can be created and assigned to one or more of the following of chronic disorders: 1) diabetes, 2) asthma, 3) hypertension, 4) a heart condition, 5) headache, and 6) a seizure disorder.

The intelligent token can also be a complex intelligent token, as explained above. The methods can be used in the context of various applications in an automated health care information system environment, including creating medical documentation, patient portal communications, and provider-to-provider communications.

While a number of exemplary aspects and embodiments have been discussed above, those of skill in the art will recognize certain modifications, permutations, additions and sub-combinations thereof may be made to the specifics of the preceding disclosure. It is therefore intended that the following appended claims, and claims hereafter introduced, are interpreted to include all such modifications, permutations, additions and sub-combinations as are within their true spirit and scope.

I claim:

1. A health care computer network system in which the manual creation of patient documentation is facilitated by automatic inclusion of information in the patient documentation based on an electronic patient medical record of the patient, comprising:
   (a) a server, by which electronic patient medical records are accessible; and
   (b) at least one computing device configured to communicate electronically with the server for accessing, through the server, the electronic patient medical records;
   (c) wherein the computing device comprises computer executable instructions contained in non-transitory computer readable medium which, when executed for generating patient documentation regarding an episode of health care services rendered to a particular patient,
   (i) provide a user interface for receiving user input regarding the episode of health services rendered for the particular patient, the user input comprising,
   (1) first user input identifying the particular patient for which the patient documentation is to be created, and
   (2) second user input for construction of the patient documentation to be created regarding the episode of health care services rendered to the particular patient, wherein the second user input includes a token comprising a character string to be replaced with information determined based on the electronic patient medical record of the particular patient,
   (ii) identify the token contained in the second user input, the token comprising a character string that is associated with a sequence of computer executable instructions for,
   (A) accessing, through the server, the electronic patient medical record for the particular patient identified by the first user input,
   (B) searching the accessed electronic patient medical record for the particular patient and identifying the existence of a chronic medical condition,
   (C) determining a duration of the chronic medical disorder by comparing onset date information to current date information,
   (D) identifying one or more associated conditions that may result from the chronic medical condition,
   (E) performing a specific search of current medications that are used to treat the chronic medical condition,
   (F) obtaining, from the electronic patient medical record, one or more recent measurement values for the patient for specific key performance indicators related to the chronic medical condition,
   (G) correlating particular data obtained in (A) through (F) to additional data and applying rules-based medical logic associated with a quality scoring system to generate, based on the particular data obtained in (A) through (F), a new result that was not previously stored in the electronic patient medical record,
   (H) inserting information including the new result in (G), in place of the identified token contained in the second user input, and
   (iii) cause the sequence of computer executable instructions associated with an identified token to be executed, when invoked, for generating the patient documentation regarding the episode of health care services rendered to the particular patient.

2. The health care computer network system of claim 1, wherein the inserted information comprises multiple items of information that is read from the electronic patient medical record of the identified patient.

3. The health care computer network system of claim 1, wherein the inserted information comprises information that is generated as a function of information that is read from the electronic patient medical record of the identified patient.

4. The health care computer network system of claim 1, wherein the inserted information comprises information that is provided from the execution of each of a plurality of other tokens.

5. The health care computer network system of claim 1, wherein the server comprises a web server and the computing devices communicate with the web server over the Internet.

6. The health care computer network system of claim 1, wherein the server comprises a database server in a computer network of a health care facility, and wherein the computing devices communicate with the database server over the computer network of the health care facility.

7. The health care computer network system of claim 1, wherein the user interface for receiving the second user input comprises a user interface for entering text by a user, and wherein a token is manually typed by a user when entering text.

8. The health care computer network system of claim 7, wherein each computing device is further configured to parse the text of the second user input entered by a user for identifying a token contained therein.

9. The health care computer network system of claim 1, wherein the user interface for receiving the second user input comprises a user interface for receiving text entered by a user, wherein the user interface presents a list of tokens that may be included in the second user input, and wherein a token is inserted into the second user input upon a user selecting the token from a list of tokens.

10. The health care computer network system of claim 1, wherein the sequence of computer executable instructions is invoked upon selection by the user of a control of the user interface for generating patient documentation.

11. The health care computer network system of claim 1, wherein the sequence of computer executable instructions is invoked upon the user causing the token to be contained in the second user input.

12. The health care computer network system of claim 11, wherein the sequence of computer executable instructions is invoked upon the user typing the character string of the token as part of the second user input.

13. The health care computer network system of claim 11, wherein the sequence of computer executable instructions is invoked upon the user typing a shorthand character string representing the token as part of the second user input.

14. The health care computer network system of claim 1, wherein the user interface that is provided further enables creation of tokens.

15. The health care computer network system of claim 1, wherein the user interface that is provided further enables creation of templates, each comprising a patient documentation construction including at least one token contained therein.

16. The health care computer network system of claim 15, wherein each token contained in the patient documentation construction of each template is invoked upon selection of the template by the user.

17. The health care computer network system of claim 1, wherein the patient documentation is in the context of physician progress notes for inpatient and ambulatory care and the user is a physician.

18. The health care computer network system of claim 1, wherein the token is associated with a disorder, and wherein the inserted information comprises a combination of at least two of: a duration of the disorder; one or more specific treatments for the disorder; one or more performance indicators associated with the disorder; and one or more grading scores.

19. The health care computer network system of claim 1, wherein the sequence of computer executable instructions associated with the token comprises the step of obtaining the latest measurement and date for specific key performance indicators.

20. The health care computer network system of claim 1, wherein the sequence of computer executable instructions associated with the token perform a review of the electronic patient medical record of the identified patient and wherein the inserted information comprises results of the review.

21. The system of claim 1, wherein the computer executable instructions contained in the non-transitory computer readable medium of the computing device are executed for each particular patient out of a plurality of patients in order to generate patient documentation regarding a respective episode of health care services rendered to each particular patient out of the plurality of patients.

22. The system of claim 1, wherein, for each particular patient out of a plurality of patients to whom health care services have been rendered, the computer executable instructions contained in the non-transitory computer readable medium of the computing device are executed following the rendering of health care services to the particular patient in order to generate the patient documentation regarding the episode of health care services rendered to the particular patient.

23. The system of claim 1, wherein the user interface comprises a text box for receiving the second user input in the form of text, which text defines a construction of the patient documentation to be created regarding the episode of health care services rendered to the particular patient.

24. The system of claim 23, wherein the text that is received in the text box for receiving the user input is typed on a keyboard by the user.

25. The system of claim 24, wherein the text that is received in the text box for receiving the user input is programmatically generated in response to a selection by the user of a control of the user interface.

26. A health care computer network system in which the manual creation of patient documentation by a health care provider is facilitated by automatic inclusion of information in the patient documentation based on an electronic patient medical record of the patient, comprising:
  (a) a server, by which electronic patient medical records are accessible; and
  (b) a computing device used by the health care provider at the point of care and configured to communicate from the point of care electronically with the server for accessing, through the server, the electronic patient medical records;
  (c) wherein the computing device comprises computer executable instructions contained in non-transitory computer readable medium which, when executed for generating at the point of care patient documentation regarding an episode of health care services rendered to a particular patient at the point of care, (i) provide a user interface for receiving at the point of care user input from the health care provider regarding the episode of health services rendered for the particular patient, the user input comprising,
(A) first user input identifying the particular patient for which the patient documentation is to be created, and
(B) second user input for construction of the patient documentation to be created regarding the episode of health care services rendered to the particular patient, wherein the second user input includes a token comprising a character string to be replaced with information determined based on the electronic patient medical record of the particular patient,
(ii) identify at the point of care the token contained in the second user input, the token comprising a character string that is associated with a sequence of computer executable instructions for,
(A) accessing from the point of care, through the server, the electronic patient medical record for the particular patient identified by the first user input,
(B) searching the accessed electronic patient medical record for the particular patient and identify the existence of a chronic medical condition,
(C) determining a duration of the chronic medical disorder by comparing onset date information to current date information,
(D) identifying one or more associated conditions that may result from the chronic medical condition,
(E) performing a specific search of current medications that are used to treat the chronic medical condition,
(F) obtaining, from the electronic patient medical record, one or more recent measurement values for the patient for specific key performance indicators related to the chronic medical condition,
(G) correlating particular data obtained in (A) through (F) to additional data and applying rules-based medical logic associated with a quality scoring system to generate, based on the particular data obtained in (A) through (F), a new result that was not previously stored in the electronic patient medical record,
(H) inserting information including the new result in (G), in place of the identified token contained in the second user input, and
(iii) cause the sequence of computer executable instructions associated with an identified token to be executed, when invoked, for generating at the point of care the patient documentation regarding the episode of health care services rendered to the particular patient.

27. The system of claim 26, wherein the computing device is a hand-held computing device.

28. The system of claim 26, wherein the computing device is a workstation computer.

29. The system of claim 26, wherein the computing device is a laptop computer.

30. The system of claim 26, wherein the health care provider is a physician.

31. The system of claim 26, wherein the health care provider is a nurse.

32. The system of claim 26, wherein the health care provider is a physician's assistant.

33. A health care computer network system in which the manual creation of patient documentation by a health care provider is facilitated by automatic inclusion of information in the patient documentation based on an electronic patient medical record of the patient, comprising:
(a) a server, by which electronic patient medical records are accessible; and
(b) a computing device used by the health care provider and configured to communicate electronically with the server for accessing, through the server, the electronic patient medical records;
(c) wherein the computing device comprises computer executable instructions contained in non-transitory computer readable medium which, when executed for generating patient documentation regarding an episode of health care services rendered to a particular patient,
(i) provide a user interface for receiving user input from the health care provider regarding the episode of health services rendered for the particular patient, the user input comprising,
(A) first user input identifying the particular patient for which the patient documentation is to be created, and
(B) second user input for construction of the patient documentation to be created regarding the episode of health care services rendered to the particular patient, wherein the second user input includes a token comprising a character string to be replaced with information determined based on the electronic patient medical record of the particular patient,
(ii) identify the token contained in the second user input, the token comprising a character string that is associated with a sequence of computer executable instructions for,
(A) accessing, through the server, the electronic patient medical record for the particular patient identified by the first user input,
(B) searching the accessed electronic patient medical record for the particular patient and identify the existence of a chronic medical condition,
(C) determining a duration of the chronic medical disorder by comparing onset date information to current date information,
(D) identifying one or more associated conditions that may result from the chronic medical condition,
(E) performing a specific search of current medications that are used to treat the chronic medical condition,
(F) obtaining, from the electronic patient medical record, one or more recent measurement values for the patient for specific key performance indicators related to the chronic medical condition,
(G) correlating particular data obtained in (A) through (F) to additional data and applying rules-based medical logic associated with a quality scoring system to generate, based on the particular data obtained in (A) through (F), a new result that was not previously stored in the electronic patient medical record,
(H) inserting information including the new result in (G), in place of the identified token contained in the second user input, and
(iii) cause the sequence of computer executable instructions associated with an identified token to be executed, when invoked, for generating the patient documentation regarding the episode of health care services rendered to the particular patient,
(iv) display on the computing device for review by the health care provider the generated patient documentation regarding the episode of health care services rendered to the particular patient, and
(v) write the generated patient documentation to the server as part of the electronic patient medical record of the patient.

34. The system of claim 33, wherein the health care provider is a physician.

35. The system of claim 33, wherein the health care provider is a nurse.

36. The system of claim 33, wherein the health care provider is a physician's assistant.

37. A health care computer network system in which the manual creation of patient documentation by a health care provider is facilitated by automatic inclusion of information in the patient documentation based on an electronic patient medical record of the patient, comprising:
- (a) a server, by which electronic patient medical records are accessible; and
- (b) a hand-held computing device used by the health care provider and configured to communicate electronically with the server for accessing, through the server, the electronic patient medical records;
- (c) wherein the hand-held computing device comprises computer executable instructions contained in nontransitory computer readable medium which, when executed for generating patient documentation regarding an episode of health care services rendered to a particular patient,
  - (i) provide a user interface for receiving user input from the health care provider regarding the episode of health services rendered for the particular patient, the user input comprising,
    - (A) first user input identifying the particular patient for which the patient documentation is to be created, and
    - (B) second user input for construction of the patient documentation to be created regarding the episode of health care services rendered to the particular patient, wherein the second user input includes a token comprising a character string to be replaced with information determined based on the electronic patient medical record of the particular patient,
  - (ii) identify the token contained in the second user input, the token comprising a character string that is associated with a sequence of computer executable instructions for,
    - (A) accessing, through the server, the electronic patient medical record for the particular patient identified by the first user input,
    - (B) searching the accessed electronic patient medical record for the particular patient and identify the existence of a chronic medical condition,
    - (C) determining a duration of the chronic medical disorder by comparing onset date information to current date information,
    - (D) identifying one or more associated conditions that may result from the chronic medical condition,
    - (E) performing a specific search of current medications that are used to treat the chronic medical condition,
    - (F) obtaining, from the electronic patient medical record, one or more recent measurement values for the patient for specific key performance indicators related to the chronic medical condition,
    - (G) correlating particular data obtained in (A) through (F) to additional data and applying rules-based medical logic associated with a quality scoring system to generate, based on the particular data obtained in (A) through (F), a new result that was not previously stored in the electronic patient medical record,
    - (H) inserting information including the new result in (G), in place of the identified token contained in the second user input, and
  - (iii) cause the sequence of computer executable instructions associated with an identified token to be executed, when invoked, for generating the patient documentation regarding the episode of health care services rendered to the particular patient.

38. The system of claim 37, wherein the health care provider is a physician.

39. The system of claim 37, wherein the health care provider is a nurse.

40. The system of claim 37, wherein the health care provider is a physician's assistant.

41. A health care computer network system in which the manual creation of patient documentation by a health care provider is facilitated by automatic inclusion of information in the patient documentation based on an electronic patient medical record of the patient, comprising:
- (a) a server, by which electronic patient medical records are accessible; and
- (b) a hand-held computing device used by the health care provider and configured to communicate electronically with the server for accessing, through the server, the electronic patient medical records;
- (c) wherein the hand-held computing device comprises computer executable instructions contained in non-transitory computer readable medium which, when executed for generating patient documentation regarding an episode of health care services rendered to a particular patient,
  - (i) provide a user interface for receiving user input from the health care provider regarding the episode of health services rendered for the particular patient, the user input comprising,
    - (A) first user input identifying the particular patient for which the patient documentation is to be created, and
    - (B) second user input for construction of the patient documentation to be created regarding the episode of health care services rendered to the particular patient, wherein the second user input includes a token comprising a character string to be replaced with information determined based on the electronic patient medical record of the particular patient,
  - (ii) identify the token contained in the second user input, the token comprising a character string that is associated with a sequence of computer executable instructions for,
    - (A) accessing, through the server, the electronic patient medical record for the particular patient identified by the first user input,
    - (B) searching the accessed electronic patient medical record for the particular patient and identify the existence of a chronic medical condition,
    - (C) determining a duration of the chronic medical disorder by comparing onset date information to current date information,
    - (D) identifying one or more associated conditions that may result from the chronic medical condition,
    - (E) performing a specific search of current medications that are used to treat the chronic medical condition,
    - (F) obtaining, from the electronic patient medical record, one or more recent measurement values for the patient for specific key performance indicators related to the chronic medical condition,
    - (G) correlating particular data obtained in (A) through (F) to additional data and applying rules-based medical logic associated with a quality scoring system to generate, based on the particular data obtained in (A) through (F), a new result that was not previously stored in the electronic patient medical record,
    - (H) inserting information including the new result in (G), in place of the identified token contained in the second user input, and
  - (iii) cause the sequence of computer executable instructions associated with an identified token to be executed, when invoked, for generating the patient documentation regarding the episode of health care services rendered to the particular patient, (iv) display on the computing device for review by the health care provider the generated patient documentation regarding the episode of health care services rendered to the particular patient, and (v) write the generated patient documentation to the server as part of the electronic health care medical record of the patient.

42. The system of claim 41, wherein the computing device is used by the health care provider at the point of care at which the episode of health care services are rendered to the particular patient following the rendering of the episode of health care services.

43. The system of claim 41, wherein the health care provider is a physician.

44. The system of claim 41, wherein the health care provider is a nurse.

45. The system of claim 41, wherein the health care provider is a physician's assistant.

* * * * *